United States Patent [19]
Abbott

[11] Patent Number: 5,429,302
[45] Date of Patent: Jul. 4, 1995

[54] NEBULIZING ELEMENT AND DEVICE

[75] Inventor: David D. Abbott, Downington, Pa.

[73] Assignee: Fisons Corporation, Rochester, N.Y.

[21] Appl. No.: 63,576

[22] Filed: May 19, 1993

[51] Int. Cl.⁶ ............................................... B05B 3/14
[52] U.S. Cl. .................... 239/102.2; 128/200.16; 310/328; 239/338
[58] Field of Search .................. 310/328; 128/200.16; 239/102.2, 338

[56] References Cited

U.S. PATENT DOCUMENTS

| | | | |
|---|---|---|---|
| 2,691,815 | 10/1954 | Boessenkool et al. | |
| 3,561,444 | 2/1971 | Boucher | 128/200.16 |
| 4,113,809 | 7/1978 | Abair et al. | 239/102.2 |
| 4,115,789 | 9/1978 | Fischbeck | 310/328 |
| 4,646,967 | 3/1987 | Geithman | 239/102.2 |
| 4,976,259 | 12/1990 | Higson et al. | 128/200.16 |
| 5,152,456 | 10/1992 | Ross et al. | 128/200.16 |
| 5,173,274 | 12/1992 | Owen | 239/102.2 |

FOREIGN PATENT DOCUMENTS

| | | | |
|---|---|---|---|
| 3029244 | 7/1982 | Germany | 128/200.16 |
| 0091414 | 8/1978 | Japan | 239/102.2 |

*Primary Examiner*—Andres Kashnikow
*Assistant Examiner*—Christopher G. Trainor
*Attorney, Agent, or Firm*—Nixon & Vanderhye

[57] ABSTRACT

There is provided a nebulizing element suitable for nebulizing a liquid, comprising:
a) oscillator means; and
b) a cover sheet;
the cover sheet being disposed between the oscillator means and the liquid to be nebulized in use; and having a metallic chemically inert layer which contacts the liquid to be nebulized in use, and a metallic energy transmission layer bonded thereto; characterized in that the metallic chemically inert layer and the metallic energy transmission layer are bonded to one another by a metallic bond. Nebulizer devices comprising such elements are also provided.

9 Claims, 1 Drawing Sheet

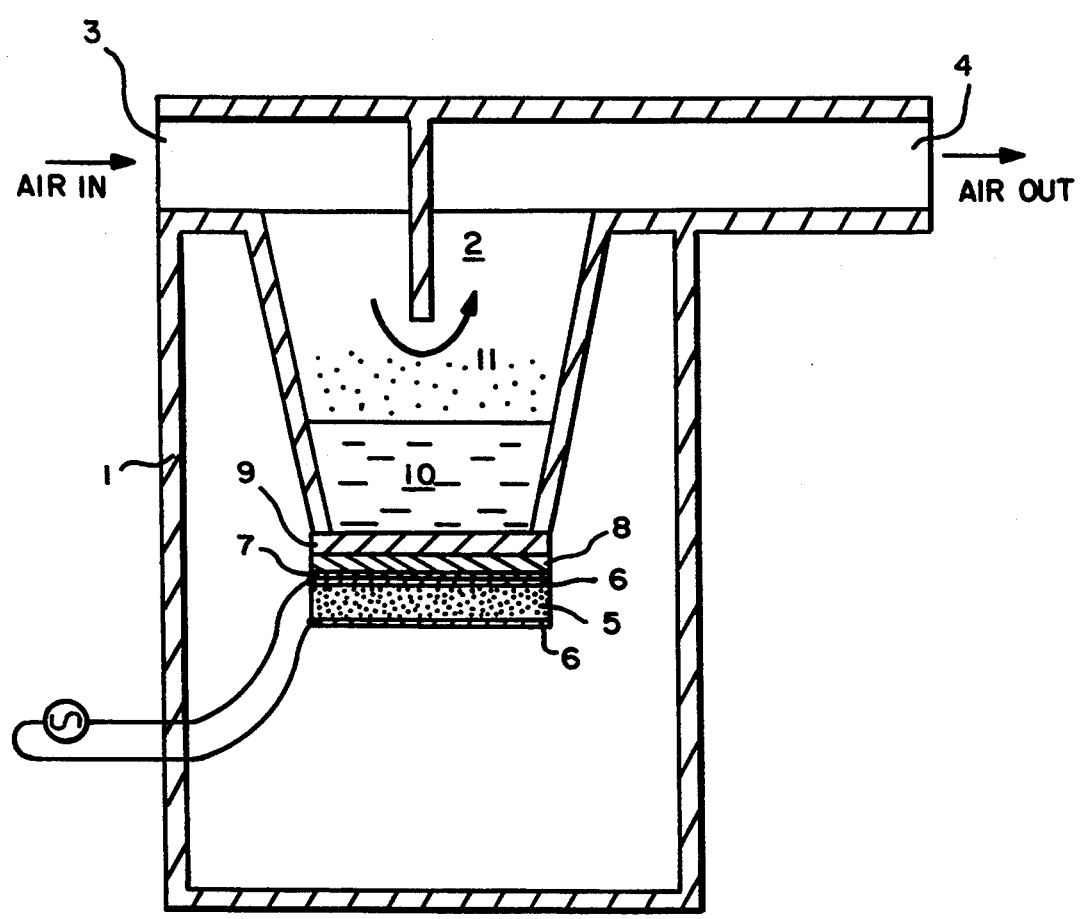

NEBULIZING ELEMENT AND DEVICE

This invention relates to a new nebulizing element suitable for nebulizing a liquid, and to devices comprising such elements.

A number of drugs are advantageously administered by inhalation to the lung (for example sodium cromoglycate and nedocromil sodium, which are useful in the treatment of asthma). In order for particles of medicament to penetrate into the lung, they should have mass median diameters of 10 $\mu$m or less. One way of administering medicament particles of this size is inhalation of an aerosol cloud containing dry powder particles of drug having the desired size. However, patients often have difficulty using aerosol devices (for example coordinating an intake of breath with emission of the aerosol cloud from the device), and the use of aerosol propellants is a matter of current environmental concern.

A second way of administering medicament particles of the desired size is by inhalation of a nebulized cloud of a solution or suspension of the drug: high frequency vibration is applied to the bottom of a small pool of solution or suspension, causing a mist of fine droplets to break away from the surface of the pool. These droplets can then be inhaled readily by a patient.

Medicament inhalation devices comprising nebulizing elements are already known (see for example U.S. Pat. No. 4,976,259 and UK Patent Application No 2224446, both to Mountain Medical Equipment Inc). Their nebulizing elements generally have oscillator means (comprising for example a slice of piezoelectric material), and a cover sheet, the cover sheet being disposed between the oscillator means and the medicament to be nebulized in use.

In a commercially available device, the cover sheet has a metallic chemically inert layer which contacts the medicament to be nebulized in use, and a metallic energy transmission layer bonded thereto. The two layers of the cover sheet are bonded together using a thermosetting resin (for example an epoxy resin), and the cover sheet is in turn bonded to the piezoelectric crystal using a thermosetting resin. A severe problem experienced with devices of this type is that the two layers of the cover sheet are prone to delaminate, leading to failure of the device. Failure of the device means that the patient cannot receive medicament, which could be fatal. There is therefore a need for a more reliable nebulizer device.

It has now been found that the two layers of the cover sheet may be securely bonded to one another by a metallic bond, which is able to withstand high frequency vibration in use, and thus allows a more reliable nebulizer device to be provided.

Thus, according to the present invention, there is provided a nebulizing element suitable for nebulizing a liquid, comprising:
a) oscillator means; and
b) a cover sheet;
the cover sheet being disposed between the oscillator means and the liquid to be nebulized in use; and having a metallic chemically inert layer which contacts the liquid to be nebulized in use, and a metallic energy transmission layer bonded thereto; characterized in that tile metallic chemically inert layer and the metallic energy transmission layer are bonded to one another by a metallic bond.

Liquids to be nebulized of particular interest are liquid medicaments. However, the nebulizing element of the present invention may be employed to produce mists of fine liquid particles in other fields, for example in elemental analysis apparatus where liquid samples are nebulized prior to atomization and analysis.

By the term "metallic bond" we mean a bond formed by attraction of atoms of one metallic layer by atoms of the other metallic layer, and vice versa. Methods for forming such bonds include friction welding, sintering and plating.

A preferred method of forming tile metallic bond is roll bonding. This means bonding of two metals by compressing them together so as to deform the metals [for example by passing between two rollers having a separation force in excess of $6.8 \times 10^5$ N ($1.5 \times 10^5$ lbs)], followed by heating so as to anneal and sinter them. The temperature chosen for sintering is preferably 55° C. (100° F.) below the melting point of the lowest melting point metal present, and the heating is preferably carried out for up to 1 hour. The process is more fully described in U.S. Pat. No. 2,691,815 and will be familiar to those skilled in the art.

Preferred features of the invention are as follows:
i) the metallic inert layer is of steel, gold, titanium or platinum, most preferably stainless steel;
ii) the metallic energy transmission layer is of aluminium, silver, magnesium or copper, most preferably aluminium;
iii) the thickness of the metallic inert layer is in the range $2.5 \times 10^{-5} - 1.0 \times 10^{-4}$ m (1/10004/1000"), for example $5'10^{-5}$ m (2/1000");
iv) the thickness of the metallic energy transmission layer is in the range $1.5 \times 10^{-4} - 6.1 \times 10^{-4}$ m (6/1000-24/1000"), for example $3 \times 10^{-4}$ m (12/1000").

The invention further provides a nebulizer device comprising a nebulizing element as defined above. Devices of particular interest are medicament inhalation devices.

The invention will now be described, by way of example, with reference to the accompanying Figure, which is a schematic sectional view of a medicament inhalation device.

A housing 1 defines an internal frusto-conical well 2 communicating with the exterior of housing 1 by means of an air inlet 3 and a mouthpiece 4. The base of well 2 is closed by a nebulizing element comprising a piezoelectric slice of lead zirconate 5, sandwiched between two silver electrodes 6. The electrodes 6 are attached to a source of alternating current.

To the upper electrode 6 is bonded, by means of a layer of epoxy resin 7, a cover sheet having a layer of aluminium 8 which is $3 \times 10^{-4}$ m (12/1000") thick and roll bonded to a layer of stainless steel 9 which is $5 \times 10^{-5}$ m (2/1000") thick. The aluminium layer 8 transmits the vibrational energy from the piezoelectric slice 5 to the liquid medicament 10 in well 2 from which it is shielded by the stainless steel layer 9.

In use, the nebulizing element vibrates with a frequency of 1.4–1.5 MHz, causing particles of liquid medicament 10 to break away from the liquid surface and form a mist of fine particles 11. These may then be inhaled into the lungs of a patient inhaling through the device at mouthpiece 4.

I claim:
1. A nebulizing element suitable for nebulizing a liquid, comprising:

a) oscillator means; and b) a cover sheet;

the cover sheet being disposed between the oscillator means and the liquid to be nebulized in use; and having a metallic chemically inert layer which contacts the liquid to be nebulized in use, and a metallic energy transmission layer bonded thereto; characterized in that the metallic chemically inert layer and the metallic energy transmission layer are bonded to one another by a metallic bond.

2. A nebulizing element as claimed in claim 1, wherein the metallic bond is formed by roll bonding.

3. A nebulizing clement as claimed in claim 1, wherein the metallic inert layer is of steel, gold, titanium or platinum.

4. A nebulizing element as claimed in claim 1, wherein the metallic energy transmission layer is of aluminium, silver, magnesium or copper.

5. A nebulizing element as claimed in claim 1, wherein the thickness of the metallic chemically inert layer is in the range $2.5 \times 10^{-5} - 1.0 \times 10^{-4}$ m (1/1000–4/1000").

6. A nebulizing element as claimed in claim 1, wherein the thickness of the metallic energy transmission layer is in the range $1.5 \times 10^{-4} - 6.1 \times 10^{-4}$ m (6/1000–24/1000").

7. A nebulizer device including a nebulizing element as claimed in claim 1.

8. A nebulizer device as claimed in claim 7 including a mouthpiece, which is a medicament inhalation device.

9. A cover sheet adapted for use in a nebulizing element as defined in claim 1.

* * * * *